United States Patent [19]

Jaeger

[11] Patent Number: 4,562,747
[45] Date of Patent: Jan. 7, 1986

[54] SAMPLER FOR DRY MATERIALS

[76] Inventor: Ben E. Jaeger, 50 Hunter La., Plano, Ill. 60545

[21] Appl. No.: 648,144

[22] Filed: Sep. 7, 1984

[51] Int. Cl.$^4$ .............................................. G01N 1/20
[52] U.S. Cl. .............................. 73/863.54; 73/863.53; 73/863.85; 73/863.86
[58] Field of Search ........... 73/863.85, 863.86, 863.82, 73/863.54, 863.53

[56] References Cited

U.S. PATENT DOCUMENTS

| 3,555,910 | 1/1971 | Spence et al. | |
|---|---|---|---|
| 3,659,461 | 5/1972 | Thompson | 73/863.54 |
| 3,747,411 | 7/1973 | McDermott et al. | 73/863.85 X |
| 3,786,682 | 1/1974 | Winter et al. | 73/863.86 |
| 4,032,395 | 6/1977 | Burnette | 73/863.86 X |
| 4,059,019 | 11/1977 | Wurster et al. | 73/863.85 X |
| 4,082,004 | 4/1978 | Weber et al. | 73/863.54 |
| 4,375,170 | 3/1983 | Sperry, III et al. | 73/863.85 |
| 4,432,674 | 2/1984 | Klose et al. | 73/863.54 X |
| 4,433,587 | 2/1984 | Risdal | 73/863.54 |
| 4,479,393 | 10/1984 | Shores | 73/863.86 X |

FOREIGN PATENT DOCUMENTS 943078  5/1956  Fed. Rep. of Germany ... 73/863.82

Primary Examiner—Stewart J. Levy
Assistant Examiner—Tom Noland
Attorney, Agent, or Firm—Gary, Juettner & Pyle

[57] ABSTRACT

A sampler for communicating with the interior of a vessel containing dry granular or powder materials extracts a sample of the material and conveys it to a point of collection. The sampler includes a tubular probe having an inlet opening toward an inner end and the probe is reciprocable into and out of the vessel for a flow of material into the inlet and through the probe to an outlet from the probe. To assist the material flow a jet of fluid is introduced into the inner end of the probe to aspirate material into the inlet opening and convey it through the probe, and when the probe is retracted from the vessel the jet purges the same of residual material. One or more valves are provided to control the jet of fluid and enable a momentary flow of fluid outwardly of the inlet opening when the probe is retracted to clear the opening of any material lodged therein.

24 Claims, 3 Drawing Figures

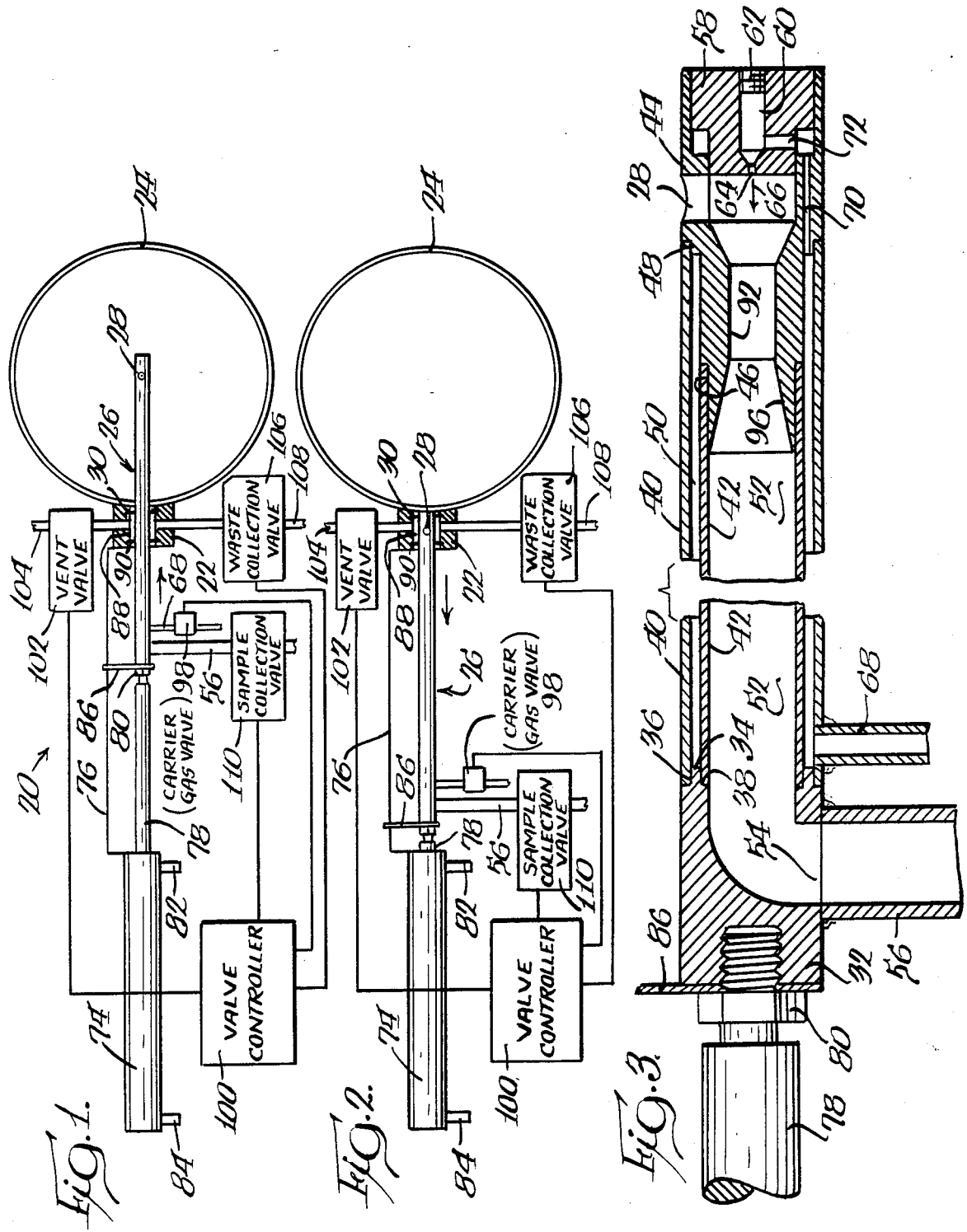

SAMPLER FOR DRY MATERIALS

BACKGROUND OF THE INVENTION

The present invention relates to apparatus for extracting samples of material from flow lines or tanks, and in particular to a sampler which is specially adapted for extracting samples of dry powder or granular materials.

Various manufacturing operations require that the immediate or overall composition of a material flowing through a pipe or conduit be monitored. Such monitoring ordinarily is accomplished with apparatus denoted as samplers, which take samples of material from the main body thereof. When a composite sample of material is required, the apparatus may be operated to withdraw a series of small amounts of the material as it passes a sampling point, which individual samples are collected and represent a composite of the total volume of material.

Other uses for samplers are in on-line analysis applications in which the immediate composition of a material must be determined. For this application, the individual samples of material are not collected as a composite sample, but instead are separately analyzed.

To obtain the samples, some samplers continuously divert material from the flow lines or tanks, and from the diverted material the samples are removed in various ways. Attempts to withdraw small quantities directly from pipes or tanks, however, have presented many problems not altogether satisfactorily solved. For example, where material receiving holes or slots in samplers are adapted to be extended directly into a pipe, sampled material can build up in such holes and slots or in the sampler itself and either block the same or contaminate subsequent samples.

Sampling dry granular or particulate materials flowing in a conveying tube under the influence of a fluid such as air or by gravity is important in the day-to-day operations of many different types of manufacturing facilities and in the handling of various types of material as for processing. To remove the granular material sample from the sample collecting apparatus, in one aspect the art contemplates using some form of conveying screw to move the sampled material into registration with a discharge chute or port. While somewhat satisfactory, screw conveyor means for emptying the sampler nevertheless is susceptible to certain disadvantages due to the frequent maintenance required as a result of material becoming lodged between the conveying screw and the tube in which it is mounted.

In accordance with another known technique, a probe having an inlet opening is extended into a product flow so that the product enters the opening and fills the probe. After the probe is filled it is retracted to expose an outlet therefrom to a discharge port, whereupon air is introduced into the probe to blow collected material out of the probe and through the port. Although the technique is satisfactory if the nature of the material is such that it readily enters the probe inlet during sampling, in many cases it is difficult if not impossible to obtain a sufficient quantity of material in the probe for sampling purposes. In addition, although the art provides various types of samplers, they are usually specially designed for the particular type and environment of material to be sampled, and are otherwise lacking in versatility.

OBJECTS OF THE INVENTION

An object of the present invention is to provide an improved sampler for dry granular or powder materials, which can operate equally well in sampling various types of materials and in any position in which it is oriented.

Another object is to provide such a sampler which cleans itself between sampling cycles.

A further object is to provide such a sampler which traverses a stream of material to be sampled to obtain a cross sectional sample thereof, and which is equally capable or moving heavy or light materials.

Yet another object is to provide a sampler which is of a design that eliminates or at least minimizes clogging and is capable of transporting sampled materials significant distances to a point of collection.

SUMMARY OF THE INVENTION

In accordance with the present invention, an apparatus for obtaining samples of product from a vessel containing the product comprises a probe having an inlet toward one end thereof for communication with the interior of the vessel and an outlet; valve means operable to establish and interrupt communication between the interior of the vessel and said inlet, whereby when communication is established a path is established for a flow of product from the vessel into said inlet, through said probe and to and through said outlet; and means for introducing a flow of fluid into said probe and along said path while communication is established to assist in moving product through said probe and to and through said outlet.

The foregoing and other objects, advantages and features of the invention will become apparent upon a consideration of the following detailed description, when taken in conjunction with the accompanying drawings.

BRIEF DESCRIPTION OF THE DRAWINGS

FIG. 1 illustrates a sampler embodying the teachings of the invention, showing the same mounted on a conduit and extended therein for obtaining a sample of dry granular or powder material flowing therethrough;

FIG. 2 is similar to FIG. 1, except that the sampler is shown retracted from the conduit; and FIG. 3 is a cross sectional side elevation view of the sampler, illustrating salient structural details thereof.

DETAILED DESCRIPTION

Referring to FIG. 1, there is indicated generally at 20 a sampler embodying the teachings of the invention. The sampler is adapted for connection through an access line or housing 22 with the interior of a vessel, conduit or pipe 24 in which is contained or through which is conveyed under influence of a fluid such as air or by gravity a dry granular or powder material. The sampler includes a probe comprising a hollow stem or plunger, indicated generally at 26, which is reciprocable through the access line for extension into the conduit for receiving a sample of material through an inlet opening 28 therein and for conveying the material to a collection point, and for retraction from the conduit at the end of the sampling operation to move the inlet to exterior of the conduit. The sampler may be cyclically reciprocated by pneumatic or electric motor means so that the collected material represents a composite sam ple of material flowing through the conduit, and a combination valve and seal means or O-ring seal 30 in the housing 22 seals the probe with the housing to prevent leakage of material from the conduit to exterior of the sampler and establishes and interrupts communication between the probe inlet and conduit interior.

Although the sampler 20 is shown connected with a conduit in which material is contained or conveyed, as will become apparent the structure and manner of operation of the sampler allows it to readily be adapted to various sampling operations and types of vessels in which material is contained. For example, it may be used to sample material in free falling streams or carried by a fluidized hopper or conveyor. It may also be used with air slide and vibratory feeding conveyors, as well for sampling material transferred through pipes under either positive or negative pressures. In addition, it is not necessary that the material to be sampled be in motion, but instead it can be in a static hopper or bin, and a particular direction of access to the material is not a prerequisite to proper operation of the sampler.

More particularly and with reference to FIG. 3, the sampler 20 is elongate and comprises the tubular probe 26 which includes at its rearward or outer end a body portion 32 having a passage therethrough and an annular lip 34 around its forward end. The lip defines annular recessed areas 36 and 38 to its opposite sides and a rearward end of a tubular sleeve 40 is extended around the outer surface of the lip within the recess 36. Extending within and coaxial with the tubular sleeve 40 is a tubular member 42, a rearward end of which is around the inner surface of the lip within the recess 38.

A forward or inner end of the probe 26 includes a tubular housing 44 which extends at its rearward end into forward ends of the tubular sleeve 40 and tubular member 42. The housing has an annular recessed area 46 at its outer end for receiving and supporting the inner end of the member, and forwardly of the recessed area the housing has another recessed area 48 in which the forward end of the sleeve is received and supported. The arrangement is such that the rearward body portion 32 and the housing support opposite ends of the sleeve and member in coaxial relationship to define a cylindrical passage 50 therebetween.

A passage extends coaxially through the forward housing 44, and along with the passages through the tubular member 42 and rearward body 32 defines a probe passage 52 extending generally axially or longitudinally through the probe. The inlet opening or port 28 is formed radially through the housing in communication with the passage 52, a rearward end of the passage communicates with an outlet opening or port 54 in the body and the outlet port connects with a sample discharge conduit 56. A path is thereby provided for a flow of material from the inlet port, through the probe passage and out of the outlet port into the conduit.

Closing the forward end of the housing 44 is a cap 58 defining a chamber 60 therein which is closed at its forward end by a threaded plug 62 and opens at its rearward end into the probe passage 52 through an orifice 64 in axial alignment with the passage. In use of the sampler, air is introduced into the chamber and emitted through the orifice in the direction of an arrow 66 along the axis of the passage, and to that end a source of air under pressure (not shown) is coupled through a line 68 to the cylindrical passage 50 between the sleeve 40 and member 42, and thence through a passage 70 in the housing to a cap passage 72 in communication with the chamber. Consequently, upon application of air under pressure through the line 68, a jet of air is emitted from the orifice for flow through the passage 52 to and through the outlet port 54 and conduit 56.

The probe 26 extends through the housing 22 and is slidably sealed therewithin by the seal means 30 for movement of the forward or inner end of the probe into and out of the conduit 24 and diametrically thereacross to obtain a sample of material. A motor means for reciprocating the probe includes an air cylinder 74 supported rearwardly of the probe by a rod or bracket 76 extending between the access line and cylinder, and a piston rod 78 of the cylinder is threaded at its forward end into the rearward body portion 32 and securely affixed thereto by a lock nut 80. The cylinder has forward and rearward air inlets 82 and 84, whereby upon introduction of air at the rearward inlet the air will act on a piston (not shown) to move the piston rod in a direction to extend the probe into the conduit, and upon introduction of air at the forward inlet the probe will be retracted from the conduit. To prevent rotation of the probe and maintain the inlet opening 28 in selected alignment with the direction of product flow, an antirotation guide plate 86 is captured at its lower end between the rearward body and nut and extends at its upper end to the rod or bracket for being slidably guided thereby.

When material is not actually being sampled, the probe 26 is retracted from the conduit 24 to a point whereat the inlet port 28 is to the outside of the seal/valve means 30 and within an annular chamber 88 in the housing 22 defined between the seal/valve means and a seal or O-ring 90, whereby communication between the inlet port and the conduit interior is interrupted. To obtain a sample of material, air is applied to the rearward air cylinder inlet 84 to drive the probe forwardly into the conduit and to move the inlet port inwardly of the valve means 30 into communication with the conduit interior. The probe is normally oriented so that the inlet port faces against the direction of material flow, although depending upon the nature of the material and its environment or the particular sampler mounting requirements other orientations of the port may be used. Ordinarily, the probe would be extended fully across and then retracted from the conduit, so that a sample of material enters the inlet port for collection, although it may just as readily be extended any selected distance into the conduit.

It is contemplated that air under pressure will be introduced through the line 68 into the probe 26 continuously during and for at least a period of time before and after the sampling operation. Consequently, when the probe is extended into the conduit, the jet of air emitted from the orifice 64 axially along the probe passage 52 and perpendicular of the axis of the inlet port 28 assists in establishing a flow of material through the inlet port and conveying the material through the probe passage to the outlet port 54 and then through the conduit 56 for collection. To that end, the air jet emitted from the orifice accomplishes two useful functions. First, by virtue of the orientation of the orifice with respect to the inlet port a negative pressure with respect to ambient is generated to the interior of the inlet port, which assists in a flow of material from the conduit into the port even when the material in the conduit is at subatmospheric pressure. Secondly, rearwardly or downstream of the inlet port there is a flow of air under positive pressure to convey the material which enters the port through the probe and to the collection point.

Consequently, because of the air flow the probe can operate equally well for substantially any orientation of the probe with respect to the conduit and/or the inlet port with respect to the material flow, and is capable of transporting sampled materials through the discharge conduit to a collection point which may be several hundred feet away from the probe. At the same time, because the probe is internally aspirated by the introduction of the air jet therein instead of being enternally aspirated by drawing air through the probe, the difference in pressure between air in the probe and ambient is not limited to atmospheric pressure and substantially any pressure of air in the probe may be generated as required for the particular sampling operation and material to be sampled.

Advantageously, the rearward end of the passage through the housing 44 may be configured to define a venturi section comprising a reduced diameter portion 92 and tapered surfaces 94 and 96 at opposite ends of the portion. Use of a venturi section results in a further reduction in pressure in the probe at the inlet port 28 to enhance a flow of material through the port, which is particularly helpful when the material in the conduit is at subatmospheric pressure. By way of example, with air at 30 psi introduced to the probe through the line 68, without the venturi section two inches of vacuum have been measured at the inlet port while with the venturi section the measured vacuum increased to twelve inches.

It is also helpful, for the purpose of controlling vacuum/pressure conditions existing in the probe 26 at and downstream of the inlet opening 28, that a valve 98 be in the air inlet line 68 for regulating the amount of air introduced into the probe. A controller 100, which may be of any suitable type and the structure of which forms no part of the present invention, may be used to operate the valve, so that in combination with a selected size of orifice 64 the valve may be opened by an amount providing predetermined vacuum/pressure conditions in the probe.

Upon retraction of the probe 26 from the conduit 24 at the end of the sample receiving cycle, the probe inlet port 28 is moved into the annular chamber 88 in the housing 22. Two openings are provided through the housing to the chamber, the first of which is coupled through a valve 102 and a line 104 to atmosphere or another source of fluid such as an inert gas, and the second of which is coupled through a valve 106 and a line 108 with a container for collecting waste material. The valves 102 and 106, along with a valve 110 in the sample discharge conduit 56, may also be connected with the controller 100 for being actuated thereby.

When the probe 26 is extended into the conduit 24, the valves 104 and 106 are closed and the valve 110 is open, so that a product sample entering the inlet port 28 is conveyed through the probe, valve 110 and line 56 for collection. However, when the probe is retracted and the inlet port is moved into the annular chamber 88, the valve 110 is momentarily closed and the valve 106 is momentarily opened so that a positive pressure of air is developed within the probe to the interior and for flow outwardly of the inlet port to clear the port of any product that may have become lodged therein during sampling, with the valve 106 then establishing an exit path from the annular chamber for product cleared from the port. After clearing the port, the valve 106 is closed and the valves 102 and 110 are opened to place the annular chamber in communication with atmosphere where the line 104 connects with atmosphere, whereupon a continued flow of air through the orifice 64, either continuously or for a limited period of time, cleans the probe passage 52 and discharge conduit 56 of any residual material remaining therein, so that no material remains to clog the probe or affect the validity of a subsequent sampling operation.

To the extent described, it has been assumed that the product sampled is compatible and may be in contact with air. However, should the product be of a type that must be kept out of contact with air, then the invention also contemplates that a supply of an inert gas such as nitrogen be connected with the lines 68 and 104. During sampling, nitrogen would then be introduced into the probe through the orifice 64, and upon retraction of the probe at the end of the sampling cycle opening of the valve 102, after the inlet port is cleared of any lodged material, would place the annular chamber 88 in communication with nitrogen. It is to be understood, of course, that irrespective of whether or not an inert gas is supplied to the probe, in addition to being supplied continuously during the actual sampling operation, the fluid need only be supplied briefly before sampling to stabilize the fluid flow through the probe and briefly after sampling to cleanse the probe and inlet port of product.

The invention thus provides an improved sampler for dry granular or powder materials, which utilizes the effect of a jet of fluid introduced into the sampler adjacent to the material entry point during the sampling process to aspirate material into and to move the material through the sampler. Because the inlet port is placed in communication with atmosphere or an inert gas at the end of each sampling cycle, the fluid jet also advantageously flushes the sampler clean of any residual material, so that there is no settling or hardening of sampled material within the sampler or contamination of subsequent samples. Although the invention has been described as being particularly advantageous for use in sampling dry granular or powder materials, the sampler may also be used with other types of materials, and it is understood that depending upon the nature of the material to be sampled a fluid other than air or an inert gas could be introduced into the sampler, for example a liquid such as water.

While embodiments of the invention have been described in detail, various modifications and other embodiments thereof may be devised by one skilled in the art without departing from the spirit and scope of the invention, as defined in the appended claims.

What is claimed is:

1. Apparatus for obtaining samples of product from a vessel, comprising a probe having an inlet for communication with the interior of the vessel and an outlet; valve means operable to establish and interrupt communication between said inlet and the interior of the vessel, whereby when communication is established a path is established for a flow of product from the vessel into said inlet, through said probe and to and through said outlet; and means for introducing a flow of fluid into said probe in proximity to said inlet and along said path when communication is established to assist in moving product into said inlet and through said probe to and through said outlet.

2. Apparatus as in claim 1, wherein said means for introducing continuously introduces said flow of fluid into said probe whenever communication is established.

3. Apparatus as in claim 1, wherein said means for introducing also introduces said flow of fluid into said probe when communication is interrupted to clean said probe of any residual sampled product.

4. Apparatus as in claim 3, wherein said valve means, upon interrupting communication between said inlet and the interior of the vessel, establishes communication between said inlet and a source of the fluid.

5. Apparatus as in claim 1, wherein said probe is tubular, said inlet is formed radially through said probe toward one end thereof and said introducing means includes means for introducing a jet of fluid into said probe adjacent to and to a side of said inlet away from said outlet, said fluid jet aspirating product from the vessel into said inlet and assisting in a flow of product through said probe to said outlet.

6. Apparatus as in claim 5, including venturi means in said probe adjacent to and to a side of said inlet toward said outlet.

7. Apparatus as in claim 5, wherein said fluid jet is introduced into said probe in a direction generally coaxial therewith.

8. Apparatus as in claim 1, wherein said valve means comprises a housing having a passage therethrough for communication with the vessel interior and in which said probe is received for reciprocation, first seal means in said passage for slidably sealing with said probe and means for reciprocating said probe in said passage to move said inlet inwardly and outwardly of said first seal means to respectively establish and interrupt communication between said inlet and the vessel interior.

9. Apparatus as in claim 8, including second seal means in said housing passage for slidably sealing with said probe outwardly of said first seal means, a chamber in said housing passage around said probe between said first and second seal means, said probe inlet entering said chamber when said inlet moves outwardly of said first seal means, an outlet in said housing from said chamber, and means for at least momentarily closing said probe outlet and for continuing to introduce said flow of fluid into said probe when said probe inlet enters said chamber so that a positive pressure of fluid in said probe flows outwardly of and through said probe inlet to clear said inlet of any product lodged therein and to convey any such product through said chamber to and through said chamber outlet.

10. Apparatus as in claim 9, wherein said means for at least momentarily closing only momentarily closes said probe outlet, and including an inlet in said housing to said chamber, means for closing said chamber inlet while said probe outlet is momentarily closed and means, after said probe outlet and chamber inlet have been momentarily closed, for opening said probe outlet and chamber inlet, closing said chamber outlet and connecting said chamber inlet with a source of the fluid, so that upon continued introduction of said flow of fluid by said introducing means said probe is cleansed of any residual sampled product therein.

11. Apparatus as in claim 1, including means for at least momentarily closing said outlet and for continuing to introduce said flow of fluid when communication is interrupted so that a positive pressure of fluid in said probe flows outwardly of and through said inlet to clear said inlet of any product lodged therein.

12. Apparatus for obtaining samples of product from a vessel, comprising a housing having a bore for communication at a forward end thereof with the interior of the vessel; a tubular probe in said bore and reciprocable therein to move a forward end of said probe toward and away from the interior of the vessel, said probe having an inlet port toward said forward end thereof and an outlet port; a combination valving and sealing means in said housing for establishing communication between said inlet port and the vessel interior when said probe is moved toward the vessel interior to establish a path for a flow of a sample of product into said inlet port, through said probe and to and through said outlet port, and for interrupting communication between said inlet port and the vessel interior when said probe is moved away from the interior of the vessel; and means for introducing a flow of fluid into said probe in proximity to said inlet port and along said path when communication is established to assist in moving product into said inlet and through said probe to and through said outlet.

13. Apparatus as in claim 12, wherein a forwardmost end of said probe is closed, said inlet port extends radially through said probe rearwardly of said closed forwardmost end, and said probe is reciprocable in said housing bore to move said inlet port inwardly and outwardly of said valving and sealing means to respectively establish and interrupt communication between said inlet port and the vessel interior.

14. Apparatus as in claim 13, including motor means for reciprocating said probe in said bore to move said inlet port to said one or said other side of said valving and sealing means to establish and interrupt communication between said inlet port and the vessel interior.

15. Apparatus as in claim 12, wherein a forwardmost end of said probe is closed and said inlet port extends radially through said probe rearwardly of said closed forwardmost end.

16. Apparatus as in claim 15, wherein said means for introducing continuously introduces said flow of fluid into said probe whenever communication is established between said inlet port and the vessel interior.

17. Apparatus as in claim 15, wherein said means for introducing also introduces said flow of fluid into said probe when communication is interrupted to clean said probe of any residual sampled product.

18. Apparatus as in claim 17, wherein said valve means, upon interrupting communication between said inlet port and the vessel interior, establishes communication between said inlet port and a source of the fluid.

19. Apparatus as in claim 15, wherein said introducing means includes means for introducing a jet of fluid into said probe forwardly of said inlet port and in a direction toward a rearward end of said probe generally along an axis thereof, said jet of fluid aspirating product from the vessel into said inlet port and assisting in a flow of product through said probe to said outlet port.

20. Apparatus as in claim 19, wherein said means for introducing comprises means for introducing a jet of air into said probe.

21. Apparatus as in claim 19, wherein said forwardmost end of said probe is closed by a cap, and said means for introducing comprises an orifice in said cap and extending generally along said probe axis and means for delivering fluid under pressure to said orifice for flow therethrough.

22. Apparatus as in claim 21, wherein said tubular probe includes an inner sleeve defining said flow path through said probe and an outer sleeve of greater diameter than, around and generally coaxial with said inner sleeve, said inner and outer sleeves forming a cylindrical passage therebetween, and said means for introducing comprises means for introducing fluid under pressure into said cylindrical passage, and passage means in said cap in communication with said cylindrical passage and orifice for conveying fluid under pressure from said cylindrical passage to said orifice.

23. Apparatus as in claim 19, including venturi means in said probe rearwardly of the point of introduction of said fluid jet therein.

24. Apparatus as in claim 23, wherein said venturi means is in said probe rearwardly of said inlet port and comprises a reduced diameter section of a passage through said probe.

* * * * *